US010336666B2

(12) United States Patent
Dziabis

(10) Patent No.: US 10,336,666 B2
(45) Date of Patent: Jul. 2, 2019

(54) PROCESSES FOR PRODUCING OLEFINS FROM PARAFFINS

(71) Applicant: UOP LLC, Des Plaines, IL (US)

(72) Inventor: Gary A. Dziabis, Addison, IL (US)

(73) Assignee: UOP LLC, des plaines, IL (US)

( * ) Notice: Subject to any disclaimer, the term of this patent is extended or adjusted under 35 U.S.C. 154(b) by 0 days.

(21) Appl. No.: 15/672,755

(22) Filed: Aug. 9, 2017

(65) Prior Publication Data

US 2019/0047922 A1 Feb. 14, 2019

(51) Int. Cl.
| C07C 5/333 | (2006.01) |
| B01J 8/08 | (2006.01) |
| B01J 8/12 | (2006.01) |
| C07C 11/06 | (2006.01) |

(52) U.S. Cl.
CPC ............. *C07C 5/333* (2013.01); *B01J 8/082* (2013.01); *B01J 8/12* (2013.01); *C07C 11/06* (2013.01); *B01J 2208/00893* (2013.01); *B01J 2208/027* (2013.01)

(58) Field of Classification Search
CPC .......... C07C 5/32; C07C 5/321; C07C 5/624; C07C 5/625; C07C 5/333; C07C 5/3332; C07C 5/3335; C07C 11/06; C07C 11/08; C07C 11/09; B01J 8/082; B01J 8/12; B01J 2208/00539; B01J 2208/00548; B01J 2208/00893; B01J 2208/027
See application file for complete search history.

(56) References Cited

U.S. PATENT DOCUMENTS

| 3,509,043 | A | * | 4/1970 | McMaster | ................ B01J 8/008 208/146 |
| 3,702,876 | A | | 11/1972 | Wood | |
| 5,489,724 | A | | 2/1996 | Harandi | |
| 5,879,537 | A | | 3/1999 | Peters | |
| 7,951,341 | B2 | | 5/2011 | Stewart et al. | |
| 2007/0122321 | A1 | * | 5/2007 | Proctor | .................. B01J 19/242 422/600 |
| 2015/0057146 | A1 | * | 2/2015 | Egolf | ....................... B01J 38/12 502/39 |
| 2015/0166424 | A1 | | 6/2015 | Vanden et al. | |

FOREIGN PATENT DOCUMENTS

| KR | 2015079957 A | 7/2015 |
| KR | 101688275 B1 | 12/2016 |

* cited by examiner

*Primary Examiner* — Brian A McCaig
*Assistant Examiner* — Jason Y Chong

(57) ABSTRACT

Processes for catalytic dehydrogenation of paraffin stream is disclosed. The process includes passing a first portion of the paraffin-containing feedstream through a select catalytic reactor in a plurality of catalytic reactors. An internal differential pressure is measured in the select catalytic reactor. A second portion of the paraffin-containing feed stream is bypassed around the select catalytic reactor when the measured internal differential pressure is above a predetermined limit of the internal differential pressure. The bypassed second portion is passed to at least one other catalytic reactor in the plurality of reactors located downstream of the select catalytic reactor being bypassed.

10 Claims, 2 Drawing Sheets

PROCESSES FOR PRODUCING OLEFINS FROM PARAFFINS

FIELD

The field of the subject matter relates to processes for producing light olefins from paraffins, and more particularly relates to a method for extending runs between maintenance shutdowns in process for producing light olefins from paraffins using catalytic dehydrogenation.

BACKGROUND

Catalytic dehydrogenation processes are commonly used for the production of light olefins by conversion from their corresponding paraffins. One specific application of this technology produces propylene from the conversion of propane. Propylene is one of the world's largest produced petrochemical commodities and is used, for example, in the production of polypropylene, acrylonitrile, acrylic acid, acrolein, propylene oxide, glycols, plasticizers, oxo alcohols, cumene, isopropyl alcohol, and acetone. Another specific application can be to produce butene from butane.

Typically, commercial process for catalytic dehydrogenation of propane includes a reactor section comprising four catalytic reactors in series wherein the propane undergoes dehydrogenation followed by a product recovery section. Such catalytic reactors unit used in catalytic dehydrogenation process commonly require maintenance shutdowns more frequently than desired because of inner and/or outer screen fouling in the reactors. The screen fouling leads to high differential pressure and maldistribution of flow. Often, either a localized void blowing event or a mechanical design limit is reached that requires that the unit be shutdown and the reactor screens cleaned/maintained. The shutdown is often about 20 to 35 days in duration with consequent lost production and execution costs. Without the issue of screen fouling, the time between turnaround could likely be increased very substantially. Existing efforts to modify process conditions to reduce the rate of fouling or alter the reactor internal design to eliminate or improve the screens have been largely unsuccessful to-date.

Therefore, there is a need for improved processes and apparatuses for efficiently to reduce the rate of screen fouling in such catalytic dehydrogenation process. There is a need for a process and an apparatus which allows extended run between costly turnarounds in such catalytic dehydrogenation processes. Other desirable features and characteristics of the present subject matter will become apparent from the subsequent detailed description of the subject matter and the appended claims, taken in conjunction with the accompanying drawings and this background of the subject matter.

SUMMARY

Various embodiments contemplated herein relate to processes for the production of light olefins from paraffins. The exemplary embodiments taught herein illustrate a process for method for extending runs between maintenance shutdowns by managing manage differential pressure increases in the reactors, in a process for producing light olefins from paraffins using catalytic dehydrogenation.

In accordance with an exemplary embodiment, a process is provided for conversion of a hydrocarbon-containing feed stream comprising passing a first portion of the hydrocarbon-containing feedstream through a select catalytic reactor in a plurality of catalytic reactors. An internal differential pressure is measured in the select catalytic reactor. A second portion of the hydrocarbon-containing feed stream is bypassed around the select catalytic reactor when the measured internal differential pressure is above a predetermined limit of the internal differential pressure. The bypassed second portion is passed to at least one other catalytic reactor in the plurality of reactors located downstream of the select catalytic reactor being bypassed.

In accordance with another exemplary embodiment, a process is provided for conversion of a hydrocarbon-containing feed stream comprising passing a first portion of the hydrocarbon-containing feedstream through a select catalytic reactor in a plurality of catalytic reactors. An internal differential pressure is measured in the select catalytic reactor using one or more analyzers and processors. The measured internal differential pressure is compared with a predetermined limit of the internal differential pressure using the one or more analyzers and processors. A valve on a bypass line is opened using a controller when the measured internal differential pressure exceeds the predetermined limit to bypass a second portion of the hydrocarbon-containing feed stream through the bypass line around the select catalytic reactor. The bypassed second portion is passed to at least one other reactor in the plurality of reactors located downstream of the select catalytic reactor being bypassed.

In accordance with yet another exemplary embodiment, a process is provided for dehydrogenation of a hydrocarbon-containing feed stream comprising passing a first portion of the hydrocarbon-containing feedstream through at a first catalytic dehydrogenation reactor to provide a first effluent stream. A first internal differential pressure is measured in the first catalytic dehydrogenation reactor and a second portion of the hydrocarbon-containing feed stream is bypassed around the first catalytic dehydrogenation reactor when the first internal differential pressure is above a first predetermined limit. A first portion of first effluent stream and at least a portion of the bypassed second portion of the hydrocarbon-containing feed stream is passed to a second catalytic dehydrogenation reactor to provide a second effluent stream. A second internal differential pressure in the second catalytic dehydrogenation reactor is measured and a second portion of first effluent stream is bypassed around the second catalytic dehydrogenation reactor when the second internal differential pressure is above a second predetermined limit. A first portion of the second effluent stream and at least one of, at least a portion of the bypassed section portion of the hydrocarbon-containing feed stream and at least a portion of the bypassed second portion of the first effluent stream, is passed to a third catalytic dehydrogenation reactor to provide a third effluent stream. A third internal differential pressure is measured in the third catalytic dehydrogenation reactor and a second portion of second effluent stream is bypassed around the third catalytic dehydrogenation reactor when the third internal differential pressure is above a third predetermined limit. A first portion of the third effluent stream and at least one of, at least a portion of the bypassed section portion of the hydrocarbon-containing feed stream, at least a portion of the bypassed second portion of the first effluent stream and at least a portion of the bypassed second portion of the second effluent stream, is passed to a fourth catalytic dehydrogenation reactor to provide a fourth effluent stream. A fourth internal differential pressure is measured in the fourth catalytic dehydrogenation reactor and a second portion of third effluent stream is bypassed around the fourth catalytic dehydrogenation reactor when the fourth internal differential pressure is above a fourth pre-determined limit.

These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following drawings, wherein like numerals denote like elements.

Figure 1:
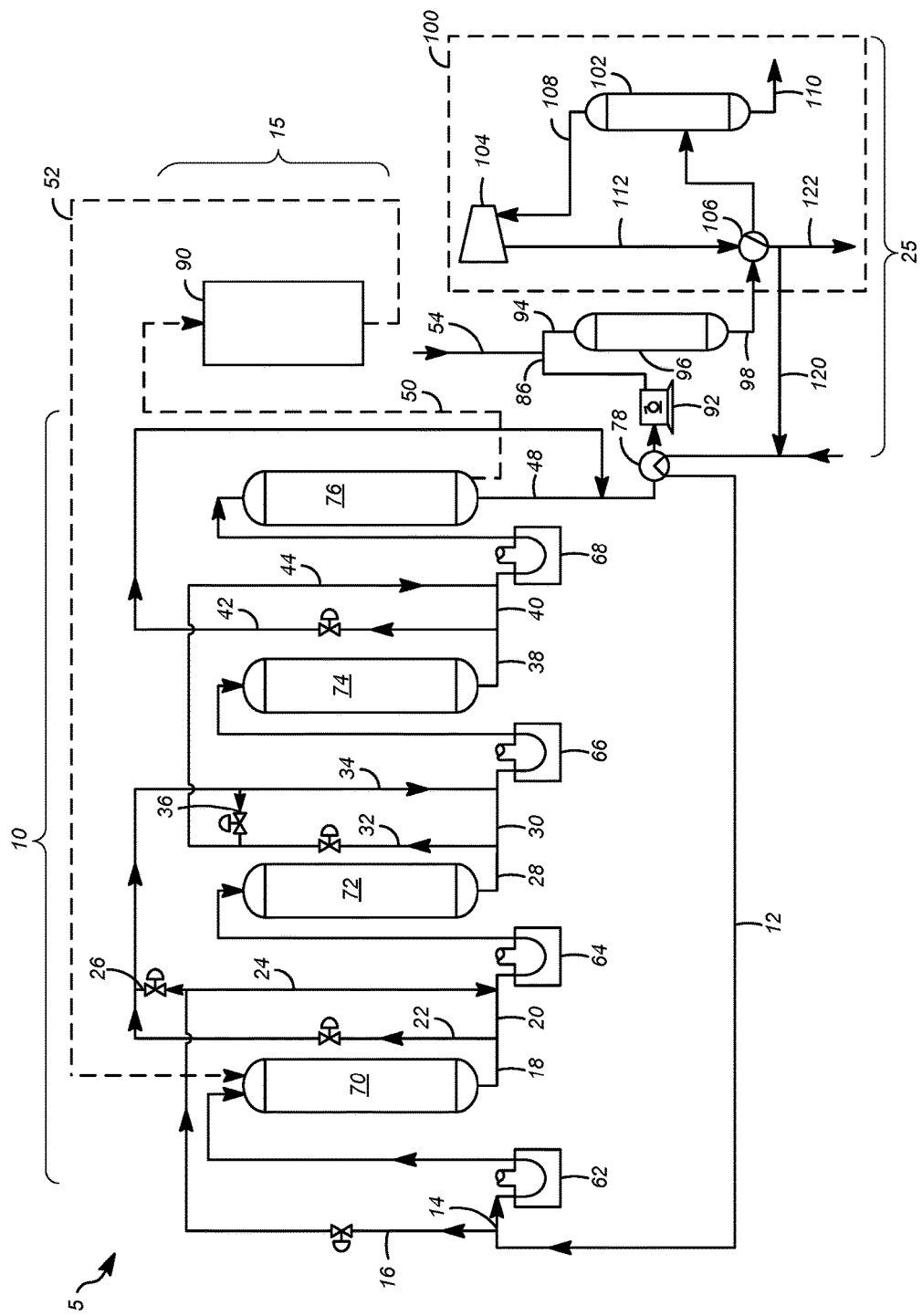
FIG. 1 illustrates a process and apparatus for catalytic dehydrogenation of paraffins according to an embodiment of the present disclosure.
Figure 2:
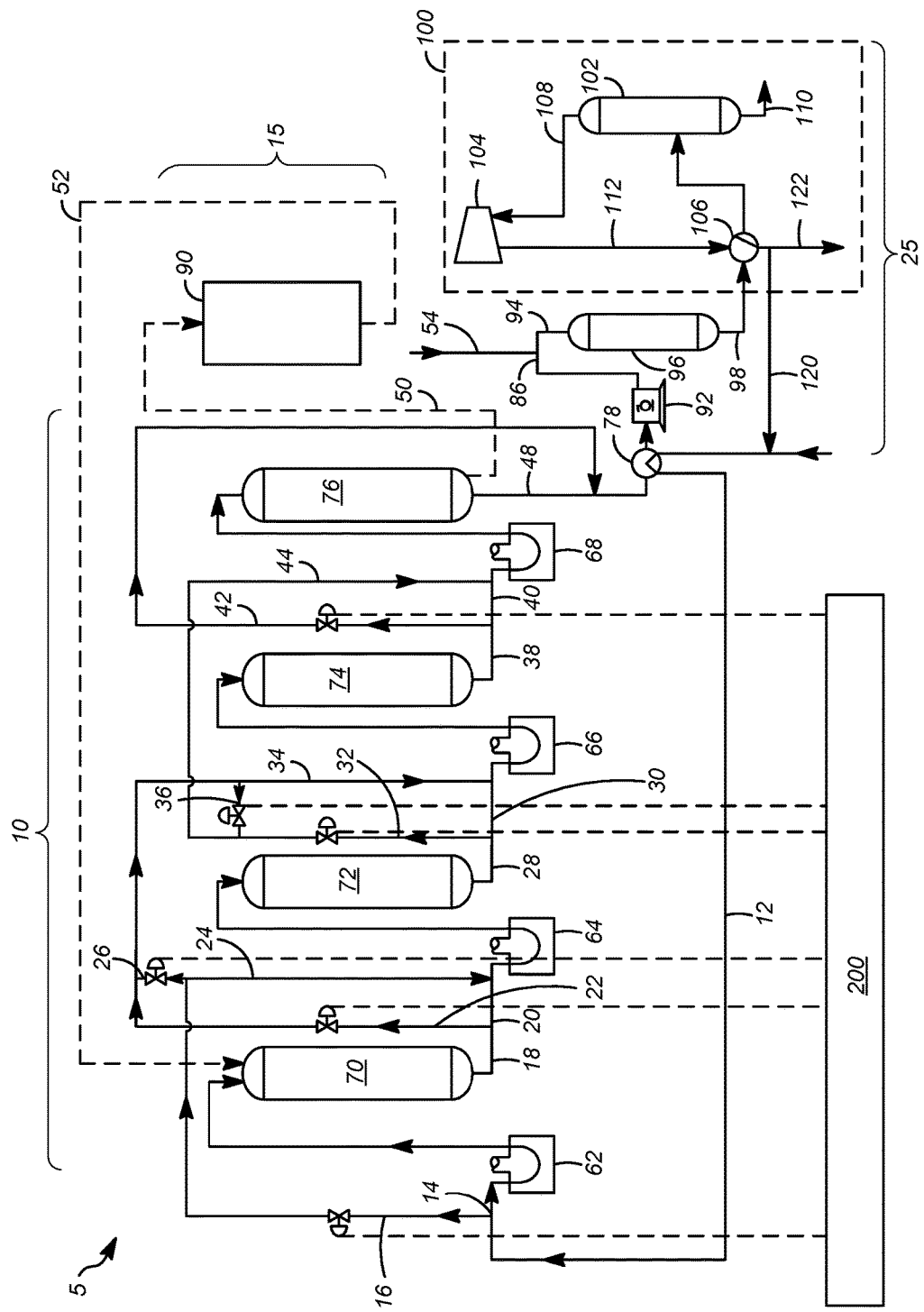
FIG. 2 illustrates a process and apparatus for catalytic dehydrogenation of paraffins according to another embodiment of the present disclosure.

Skilled artisans will appreciate that elements in FIGS. 1 and 2 are illustrated for simplicity and clarity and have not necessarily been drawn to scale. For example, the dimensions of some of the elements in FIGS. 1 and 2 may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

Various embodiments herein relate to processes for producing light olefins from paraffins such as propylene from propane. A fresh feed is introduced to a series of paraffin dehydrogenation reactors that contain dehydrogenation catalyst and are operating at dehydrogenation conditions to produce an effluent. The effluent contains propylene, unconverted propane, hydrogen, and various other hydrocarbons such as $C_{2-}$, $C_{4+}$, and some dienes and alkynes. As used herein, $C_x$ means hydrocarbon molecules that have "X" number of carbon atoms, $C_{x+}$ means hydrocarbon molecules that have "X" and/or more than "X" number of carbon atoms, and $C_{x-}$ means hydrocarbon molecules that have "X" and/or less than "X" number of carbon atoms.

The process provides flexibility in bypassing one or more reactors in a four reactor set up in a typical propane dehydrogenation process. The process includes the addition of bypass lines with control elements that could be partially or fully opened to divert some portion of the process flow around a select catalytic reactor(s), in a plurality of reactors, experiencing the fastest or greatest degree of screen fouling. As used herein, the term "select catalytic reactor", is not limited to single catalytic reactor and may include two or more reactors in the plurality of reactors. In the process, a first portion of the hydrocarbon-containing feedstream may be passed through the select catalytic reactor in a plurality of catalytic reactors. An internal differential pressure in the select catalytic reactor may be constantly or periodically measured. A second portion of the hydrocarbon-containing feed stream may be bypassed around the select catalytic reactor when the measured internal differential pressure is above a predetermined limit of the internal differential pressure. The bypassed second portion may be passed to at least one other catalytic reactor in the plurality of reactors located downstream of the select catalytic reactor being bypassed. Consequently, the void blowing margin for the select catalytic reactor would be increased due to lower volumetric flow through the select catalytic reactor. Likewise, the differential pressure through the select catalytic reactor being bypassed would decrease, moving away from any mechanical design limitation. An inlet temperatures of the at least one other reactor in the plurality of reactors may be raised to at least partially compensate for the lost conversion from partially bypassing the select catalytic reactor.

In one embodiment, the internal differential pressure being measured may be differential pressure across an inner screen in the select catalytic reactor. In such an embodiment, the predetermined limit of the internal differential pressure across the inner screen may be from about 3.5 kPa to about 5 kPa, or from about 4 to about 4.5 kPa. In another embodiment, the internal differential pressure is differential pressure across an outer screen in the select catalytic reactor. In such an embodiment, the predetermined limit of the internal differential pressure across the outer screen may be from about 68 kPa to about 104 kPa, or from about 75 to about 90 kPa.

Referring now to FIG. 1 which shows one typical arrangement for a moving bed dehydrogenation process 5. The process 5 includes a reactor section 10, a regeneration section 15, and a product recovery section 20. The reactor section 10 may include a plurality of reactors in series as shown in FIG. 1, the reactor section 10 may include four reactors including a first catalytic reactor 70, a second catalytic reactor 72, a third catalytic reactor 74 and a fourth catalytic reactor 76. The reactor section 10 may further comprises four reactor feed heaters including a first reactor feed heater 62, a second reactor feed heater 64, a third reactor feed heater 66 and a fourth reactor feed heater 68. As shown in FIG. 1, the four catalytic reactors and reactor feed heaters are alternately connected in series. Each of the four catalytic reactor 70, 72, 74, and 76 contain dehydrogenation catalyst, e.g., platinum-containing catalyst and the like, and are configured to advance the dehydrogenation catalyst as moving beds between the catalytic reactors 70, 72, 74, and 76. Other reactor arrangements for dehydrogenation of paraffins, such as, for example, swing bed reactor arrangements and the like may also be used. The four catalytic reactors 70, 72, 74, and 76 are operating at a temperature of from about 575 to about 675° C. and at a relatively low pressure of about 100 kPa to about 150 kPa. Each of the four catalytic reactors can operate at different temperature and pressures within the above specified range.

In accordance with an exemplary embodiment, a hydrocarbon-containing feed stream in line 12 may be passed to the reactor section 5 where it is subsequently passed through the plurality of reactors 70, 72, 74 and 76 to undergo dehydrogenation. For the purpose of discussion herein, the hydrocarbon-containing feed stream may be a feed stream comprising propane and may be interchangeably referred to as the propane feed stream. A hydrogen recycle stream in line 120 may also be provided to the reactor section 5 as described later. The valve on a bypass line 16 may be open or closed. In one embodiment, the valve on bypass line 16 may be open. In such an embodiment, a first portion of the hydrocarbon-containing feedstream may be passed in line 14 to a first catalytic reactor 70 to provide a first effluent stream in line 18. As shown, the first portion of the hydrocarbon-containing feed stream in line 14 may be passed through the first reactor feed heater 62 before being passed to the first catalytic reactor 70. A second portion of the hydrocarbon-containing feed stream may be passed through the bypass line 16. As shown in FIG. 1, the second portion may be taken from the hydrocarbon-containing feedstream upstream of the first reactor feed heater 62. In an alternate embodiment, the second portion may be taken downstream (not shown) of the first reactor feed heater. A first effluent stream in line 18 may be withdrawn from the first catalytic reactor 70. In operation, a first internal differential pressure in the first catalytic reactor may be measured continuously or intermittently using one or more analyzers and processors. The measured first internal differential pressure is compared with a predetermined limit of the first internal differential pressure using the one or more analyzers and processors. The valve on the bypass line 16 may be opened when the measured first internal differential pressure exceeds the predetermined limit of the first internal differential pressure to bypass the second portion of the hydrocarbon-containing feed stream through the bypass line 16 around the first catalytic reactor 70. The bypassed second portion may be introduced to at least one of second catalytic reactor 72, the third catalytic reactor 74 and the fourth catalytic reactor 76 as describe in detail below.

The first effluent stream in line 18 comprising partially reacted propane stream may be passed to the second catalytic reactor 72. The first effluent stream in line 18 may be passed through the second reactor feed heater 64 before being passed to the second catalytic reactor 72. The valve on a bypass line 22 may be open or closed. In one embodiment, the valve on the bypass line 22 may be open and a first portion of the first effluent stream may be passed in line 20 to the second catalytic reactor 72. Further, at least a portion of the bypassed second portion of the hydrocarbon-containing feed stream in line 24 may be passed to the second catalytic reactor 72. The valve on line 26 may be open or closed. In an embodiment, when the valve on line 26 is open, a remaining portion of the bypassed second portion of the hydrocarbon-containing feed stream may be passed to downstream reactors. In other embodiments, when the valve on line 26 is closed, the bypassed second portion of the hydrocarbon containing feed stream may be passed completely to the second catalytic reactor 72. A second portion of the first effluent may be passed through the bypass line 22. As shown in FIG. 1, the second portion may be taken from the first effluent stream upstream of the second reactor feed heater 64. In an alternate embodiment, the second portion may be taken downstream (not shown) of the second reactor feed heater. A second effluent stream in line 28 may be withdrawn from the second catalytic reactor 72. In operation, a second internal differential pressure in the second catalytic reactor may be measured continuously using one or more analyzers and processors. The measured second internal differential pressure is compared with a predetermined limit of the second internal differential pressure using the one or more analyzers and processors. The valve on the bypass line 22 may be opened when the measured second internal differential pressure exceeds the predetermined limit of the second internal differential pressure to bypass the second portion of the first effluent stream through the bypass line 22 around the second catalytic reactor 72.

The second effluent stream in line 28 may be passed to the third catalytic reactor 74. The second effluent stream in line 28 may be passed through the third reactor feed heater 66 before being passed to the third catalytic reactor 74. The valve on a bypass line 32 may be open or closed. In accordance with an exemplary embodiment, the valve on the bypass line 32 may be open. In such an embodiment, a first portion of the second effluent stream may be passed in line 30 to the third catalytic reactor 74. Further, at least a portion of the bypassed second portion of the first effluent stream in line 34 may be passed to the third catalytic reactor 74. The valve on line 36 may be open or closed. In an embodiment, when the valve on line 36 is open, the remaining portion of the bypassed second portion of the first effluent stream may be passed to downstream reactors. In other embodiments, when the valve on line 36 is closed, bypassed second portion of the first effluent stream may be completely passed to the third catalytic reactor 74. Additionally, a portion of the bypassed second portion of the hydrocarbon-containing feed stream in line 26 may be passed to the third catalytic reactor 74. A second portion of the second effluent may be passed through the bypass line 32. As shown, the second portion may be taken from the second effluent stream upstream of the third reactor feed heater 66. In an alternate embodiment, the second portion may be taken downstream (not shown) of the third reactor feed heater 66. A third effluent stream in line 38 may be withdrawn from the third catalytic reactor 74. In operation, a third internal differential pressure in the third catalytic reactor 74 may be measured continuously using one or more analyzers and processors. The measured third internal differential pressure is compared with a predetermined limit of the third internal differential pressure using the one or more analyzers and processors. The valve on the bypass line 32 may be opened when the measured third internal differential pressure exceeds the predetermined limit of the third internal differential pressure to bypass the second portion of the second effluent stream through the bypass line 32 around the third catalytic reactor 74.

The third effluent stream in line 38 may be passed to the fourth catalytic reactor 76. The third effluent stream in line 38 may be passed through the fourth reactor feed heater 68 before being passed to the fourth catalytic reactor 76. The valve on a bypass line 42 may be open or closed. In accordance with an exemplary embodiment, the valve on the bypass line 42 may be open. In such an embodiment, a first portion of the third effluent stream may be passed in line 40 to the fourth catalytic reactor 76. Further, at least a portion of the bypassed second portion of the second effluent stream in line 44 may be passed to the fourth catalytic reactor 76. Further, at least a portion of bypass around any of the upstream reactors may also be passed to the fourth catalytic reactor 76. For example, at least a portion of the bypassed section portion of the hydrocarbon-containing feed stream and/or at least a portion of the bypassed second portion of the first effluent stream may be passed to the fourth catalytic reactor 76. A second portion of the third effluent stream may be passed through the bypass line 42. As shown in FIG. 1, the second portion may be taken from the third effluent stream upstream of the fourth reactor feed heater 68. In an alternate embodiment, the second portion may be taken downstream (not shown) of the fourth reactor feed heater 68. A fourth effluent stream in line 48 may be withdrawn from the fourth catalytic reactor 76. In operation, a fourth internal differential pressure in the fourth catalytic reactor 76 may be measured continuously, periodically or intermittently using one or more analyzers and processors. The measured fourth internal differential pressure is compared with a predetermined limit of the fourth internal differential pressure using the one or more analyzers and processors. The valve on the bypass line 42 may be opened when the measured fourth internal differential pressure exceeds the predetermined limit of the fourth internal differential pressure to bypass the second portion of the third effluent stream through the bypass line 42 around the fourth catalytic reactor 76 and processed together with the fourth effluent stream.

In an embodiment, one or more of the first, second, third and fourth internal differential pressure being measured may be the differential pressure measured across an inner screen in the respective catalytic reactor. In such an embodiment, the predetermined limit of the internal differential pressure across the inner screen may be from about 3.5 kPa to about 5 kPa, or from about 4 to about 4.5 kPa. In another embodiment, one or more of the first, second, third and fourth internal differential pressure being measured may be the differential pressure measured across an outer screen in the respective catalytic reactor. In such an embodiment, the predetermined limit of the internal differential pressure across the outer screen may be from about 68 kPa to about 104 kPa, or from about 75 to about 90 kPa.

In an embodiment, the fourth effluent stream contains propylene, unconverted propane, hydrogen, and various other hydrocarbons such as $C_{2-}$, $C_{4+}$, and some dienes and alkynes. Although not shown, partially spent dehydrogenation catalyst may be transferred from the first catalytic reactor 70 progressively to each of the next catalytic reactors 72, 74, and 76 in a moving bed fashion for further conversion of propane to propylene, and is then sent in line 50 to a regeneration unit 90 present in the regeneration section 15 for regeneration of the spent dehydrogenation catalyst. The regenerated dehydrogenation catalyst is then transferred in line 52 from the regeneration unit 90 back to the first catalytic reactor 70 to replenish partially spent catalyst that is being removed from the first catalytic reactor 70.

As illustrated in FIG. 1, the fourth effluent stream in line 48 may be passed from the reactor section 10 to the product recovery section 25 where the effluent is partially cooled via a heat exchanger 78. The fourth effluent stream is then passed to a compressor 92 that compresses the effluent to a predetermined high pressure. In an exemplary embodiment, the fourth effluent stream is compressed to a predetermined high pressure of from about 1,000 to about 2,000 kPa.

An off-gas stream in line 54 may be combined with the fourth effluent stream in line 48 in the product recovery section 25 to form a combined effluent stream in line 94. In an exemplary embodiment, the off-gas stream in line 54 is at about the same pressure or greater than the pressure of the fourth effluent stream after being compressed to the predetermined high pressure. Preferably, the off-gas stream in line 54 may be combined with the fourth effluent stream downstream from the compressor 92 as illustrated. However, although the off-gas stream 54 is shown as being combined with the effluent 86 downstream from the compressor 92, it should be understood that the off-gas stream 54 can alternatively be combined with the fourth effluent stream 48 upstream from the compressor 92.

The combined effluent stream in line 94 may be dried and treated by removing any chloride containing compounds using a chloride treater and dryer unit 96 to provide a treated combined effluent stream in line 98. The treated combined effluent stream 94 is then passed along to the cold box section 100 of the product recovery section 25. As illustrated, the cold box section 100 comprises a separator 102, an expander 104, and a heat exchanger 106 that are cooperatively configured to cryogenically cool the treated combined effluent stream in line 98. In particular, hydrogen is removed from the treated combined effluent stream, which is a mixed vapor-liquid phase, downstream in the separator 102 as, for example, an overhead stream in line 108 and is expanded via the expander 102 to form a chilled hydrogen stream in line 112. The upstream combined effluent stream 94 is cryogenically cooled via indirect heat exchange with the treated combined effluent stream in line 98 in the heat exchanger 104 and is removed from the product recovery section 25 as, for example, a liquid bottom stream in line 110 from the separator 102. In an exemplary embodiment, the treated combined effluent stream is cooled to a temperature of from about −130 to about −150° C. As illustrated, the chilled hydrogen stream in line 112 is split downstream from the heat exchanger 106 into the hydrogen recycle stream 120 that is combined with the propane feed stream to provide fuel for the first reactor feed heater 62, and a second hydrogen stream 122.

The subject process comprises feeding fresh propane to a paraffin dehydrogenation reactor that contains dehydrogenation catalyst and is operating at dehydrogenation conditions to produce an effluent containing propylene, unconverted propane, hydrogen, and various other hydrocarbons such as $C_{2-}$, $C_{4+}$, and some dienes and alkynes. However, the apparatus and process as disclosed in the present disclosure employs bypass lines to divert some portion of reactor feed around one or more reactors experiencing the fastest or greatest degree of screen fouling. Consequently, the void blowing margin for the bypassed reactor would be increased due to lower volumetric flow through the reactor. Likewise, the differential pressure through the bypassed reactor would decrease, moving away from any mechanical design limitation. The bypassed portion of the reactor feed would be reintroduced downstream of the bypassed reactor so that the downstream reactors could still achieve a substantial conversion of this bypassed portion. In the case of bypassing the last reactor, the uncoverted portion of the feed that bypassed this reactor could be recovered in the downstream separation system and recycled for another pass through the reactors. Consequently, the unconverted feed is not lost. The increased utilities associated with recycling more unconverted feed is economically justified in comparison to the improved economics associated with a significantly extended run between costly turnarounds.

FIG. 2 illustrates another exemplary embodiments of the process including a computer 200 in communication with the process 5. As shown in FIG. 2, the valves on the various bypass line including valves on bypass line 16, 22, 26, 32, 36 and 42 are in communication with the computer 200 which automatically controls the operation of the valves through one or more control modules including processors and analyzers. The computer 200 through its one or more control modules measures the internal differential pressure of each of the catalytic reactor. Further, the control modules compare the measured internal differential pressure with a predetermined limit of the internal differential pressure using the one or more analyzers and processors. The valve on a bypass line around a select catalytic reactor(s) may be regulated using the control modules. For example, the valve on the bypass line is opened automatically when the measured internal differential pressure exceeds the predetermined limit to bypass a portion of the hydrocarbon-containing feed stream through the bypass line around the select catalytic reactor. Similarly, the valve on the bypass line is kept closed when the measured internal differential pressure of the select catalytic reactor is below the predetermined limit of the internal differential pressure. The degree to which the valve is opened may also be controlled in the same fashion.

In some embodiments, various functions described herein may be implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), Blu-ray or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Specific Embodiments

While the following is described in conjunction with specific embodiments, it will be understood that this description is intended to illustrate and not limit the scope of the preceding description and the appended claims.

A first embodiment of the invention is a process for conversion of a hydrocarbon-containing feed stream comprising passing a first portion of the hydrocarbon-containing feedstream through a select catalytic reactor in a plurality of catalytic reactors; measuring an internal differential pressure in the select catalytic reactor; bypassing a second portion of the hydrocarbon-containing feed stream around the select catalytic reactor when the measured internal differential pressure is above a predetermined limit of the internal differential pressure; and passing the bypassed second portion to at least one other catalytic reactor in the plurality of reactors located downstream of the select catalytic reactor being bypassed. An embodiment of the invention is one, any or all of prior embodiments in this paragraph up through the first embodiment in this paragraph, wherein the internal differential pressure is differential pressure across an inner screen in the catalytic reactor. An embodiment of the invention is one, any or all of prior embodiments in this paragraph up through the first embodiment in this paragraph, wherein the predetermined limit of the internal differential pressure across the inner screen is about 3.5 kPa to about 5 kPa. An embodiment of the invention is one, any or all of prior embodiments in this paragraph up through the first embodiment in this paragraph, wherein the internal differential pressure is differential pressure across an outer screen in the catalytic reactor. An embodiment of the invention is one, any or all of prior embodiments in this paragraph up through the first embodiment in this paragraph, wherein the predetermined limit of the internal differential pressure across the outer screen is about 68 kPa to about 104 kPa. An embodiment of the invention is one, any or all of prior embodiments in this paragraph up through the first embodiment in this paragraph, wherein each of the catalytic reactor in the plurality of reactors has an upstream reactor feed heater. An embodiment of the invention is one, any or all of prior embodiments in this paragraph up through the first embodiment in this paragraph, wherein the second portion is bypassed upstream of the reactor feed heater of the select catalytic reactor. An embodiment of the invention is one, any or all of prior embodiments in this paragraph up through the first embodiment in this paragraph, wherein the second portion is bypassed downstream of the reactor feed heater of the select catalytic reactor. An embodiment of the invention is one, any or all of prior embodiments in this paragraph up through the first embodiment in this paragraph, wherein the bypassed second portion is introduced upstream of the reactor feed heater of the at least one other catalytic reactor. An embodiment of the invention is one, any or all of prior embodiments in this paragraph up through the first embodiment in this paragraph, wherein the bypassed second portion is introduced downstream of the reactor feed heater of the at least one other catalytic reactor. An embodiment of the invention is one, any or all of prior embodiments in this paragraph up through the first embodiment in this paragraph, wherein the internal differential pressure in the select catalytic reactor is measured using one or more analyzers and processors and the measured internal differential pressure is compared with the predetermined limit of the internal differential pressure. An embodiment of the invention is one, any or all of prior embodiments in this paragraph up through the first embodiment in this paragraph further comprising opening a valve on a bypass line using a controller when the measured internal differential pressure exceeds the predetermined limit to bypass the second portion of the hydrocarbon-containing feed stream around the select catalytic reactor. An embodiment of the invention is one, any or all of prior embodiments in this paragraph up through the first embodiment in this paragraph, wherein the process is catalytic dehydrogenation of the hydrocarbon-containing feed stream.

A second embodiment of the invention is a process for conversion of a hydrocarbon-containing feed stream comprising passing a first portion of the hydrocarbon-containing feedstream through a select catalytic reactor in a plurality of catalytic reactors; measuring an internal differential pressure in the select catalytic reactor using one or more analyzers and processors; comparing the measured internal differential pressure with a predetermined limit of the internal differential pressure using the one or more analyzers and processors; opening a valve on a bypass line using a controller when the measured internal differential pressure exceeds the predetermined limit to bypass a second portion of the hydrocarbon-containing feed stream through the bypass line around the select catalytic reactor; and passing the bypassed second portion to at least one other reactor in the plurality of reactors located downstream of the select catalytic reactor being bypassed. An embodiment of the invention is one, any or all of prior embodiments in this paragraph up through the second embodiment in this paragraph, wherein the internal differential pressure is differential pressure across an inner screen in the catalytic reactor. An embodiment of the invention is one, any or all of prior embodiments in this paragraph up through the second embodiment in this paragraph, wherein the predetermined limit of the internal differential pressure across the inner screen is about 3.5 kPa to about 5 kPa. An embodiment of the invention is one, any or all of prior embodiments in this paragraph up through the second embodiment in this paragraph, wherein the internal differential pressure is differential pressure across an outer screen in the catalytic reactor. An embodiment of the invention is one, any or all of prior embodiments in this paragraph up through the second embodiment in this paragraph, wherein the predetermined limit of the internal differential pressure across the outer screen is about 68 kPa to about 104 kPa.

A third embodiment of the invention is a process for dehydrogenation of a hydrocarbon-containing feed stream comprising passing a first portion of the hydrocarbon-containing feedstream through at a first catalytic dehydrogenation reactor to provide a first effluent stream; measuring a first internal differential pressure in the first catalytic dehydrogenation reactor and bypassing a second portion of the hydrocarbon-containing feed stream around the first catalytic dehydrogenation reactor when the first internal differential pressure is above a first predetermined limit; passing a first portion of first effluent stream and at least a portion of the bypassed second portion of the hydrocarbon-containing feed stream to a second catalytic dehydrogenation reactor to provide a second effluent stream; measuring a second internal differential pressure in the second catalytic dehydrogenation reactor and bypassing a second portion of first effluent stream around the second catalytic dehydrogenation reactor when the second internal differential pressure is above a second predetermined limit; passing a first portion of the second effluent stream and at least one of, at least a portion of the bypassed section portion of the hydrocarbon-containing feed stream and at least a portion of the bypassed second portion of the first effluent stream, to a third catalytic dehydrogenation reactor to provide a third effluent stream; measuring a third internal differential pressure in the third catalytic dehydrogenation reactor and bypassing a second portion of second effluent stream around the third catalytic dehydrogenation reactor when the third internal differential pressure is above a third predetermined limit; passing a first portion of the third effluent stream and at least one of, at least a portion of the bypassed section portion of the hydrocarbon-containing feed stream, at least a portion of the bypassed second portion of the first effluent stream and at least a portion of the bypassed second portion of the second effluent stream, to a fourth catalytic dehydrogenation reactor to provide a fourth effluent stream; and measuring a fourth internal differential pressure in the fourth catalytic dehydrogenation reactor and bypassing a second portion of third effluent stream around the fourth catalytic dehydrogenation reactor when the fourth internal differential pressure is above a fourth pre-determined limit. An embodiment of the invention is one, any or all of prior embodiments in this paragraph up through the third embodiment in this paragraph further comprising passing the bypassed second portion of the third effluent stream to downstream separation process to recover unconverted hydrocarbon-containing feed stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for dehydrogenation of a hydrocarbon-containing feed stream comprising:
   a) passing a first portion of the hydrocarbon-containing feedstream through at a first catalytic dehydrogenation reactor to provide a first effluent stream, the hydrocarbon-containing feedstream comprising propane, butane, or a combination thereof;
   b) measuring a first internal differential pressure across a first screen or a second screen in the first catalytic dehydrogenation reactor and bypassing a second portion of the hydrocarbon-containing feed stream around the first catalytic dehydrogenation reactor when the first internal differential pressure is above a first predetermined limit;
   c) passing a first portion of first effluent stream and at least a portion of the bypassed second portion of the hydrocarbon-containing feed stream to a second catalytic dehydrogenation reactor to provide a second effluent stream;
   d) measuring a second internal differential pressure across a first screen or a second screen in the second catalytic dehydrogenation reactor and bypassing a second portion of the first effluent stream around the second catalytic dehydrogenation reactor when the second internal differential pressure is above a second predetermined limit;
   e) passing a first portion of the second effluent stream and at least one of, at least a portion of the bypassed section portion of the hydrocarbon-containing feed stream and at least a portion of the bypassed second portion of the first effluent stream, to a third catalytic dehydrogenation reactor to provide a third effluent stream;
   f) measuring a third internal differential pressure across a first screen or a second screen in the third catalytic dehydrogenation reactor and bypassing a second portion of the second effluent stream around the third catalytic dehydrogenation reactor when the third internal differential pressure is above a third predetermined limit;
   g) passing a first portion of the third effluent stream and at least one of, at least a portion of the bypassed section portion of the hydrocarbon-containing feed stream, at least a portion of the bypassed second portion of the first effluent stream and at least a portion of the bypassed second portion of the second effluent stream, to a fourth catalytic dehydrogenation reactor to provide a fourth effluent stream; and
   h) measuring a fourth internal differential pressure across a first screen or a second screen in the fourth catalytic dehydrogenation reactor and bypassing a second portion of the third effluent stream around the fourth catalytic dehydrogenation reactor when the fourth internal differential pressure is above a fourth predetermined limit
   wherein the first, second, third, and fourth catalytic dehydrogenation reactors are moving bed reactors and are arranged in series.

2. The process of claim 1 further comprising passing the bypassed second portion of the third effluent stream to a downstream separation process to recover unconverted hydrocarbon-containing feed stream.

3. The process of claim 1, wherein the predetermined limit of the internal differential pressure across the first screen of each catalytic dehydrogenation reactor is about 3.5 kPa to about 5 kPa.

4. The process of claim 1, wherein the predetermined limit of the internal differential pressure across the second screen of each catalytic dehydrogenation reactor is about 68 kPa to about 104 kPa.

5. The process of claim 1, wherein each of the catalytic dehydrogenation reactors has an upstream reactor feed heater.

6. The process of claim 5, wherein the second portion of the hydrocarbon-containing feedstream is bypassed upstream of the reactor feed heater of the first catalytic dehydrogenation reactor.

7. The process of claim 5, wherein the second portion of the hydrocarbon-containing feedstream is bypassed downstream of the reactor feed heater of the first catalytic dehydrogenation reactor.

8. The process of claim 5, wherein the bypassed second portion of the hydrocarbon-containing feedstream is introduced upstream of the reactor feed heater of at least one other catalytic dehydrogenation reactor.

9. The process of claim 5, wherein the bypassed second portion of the hydrocarbon-containing feedstream is introduced downstream of the reactor feed heater of at least one other catalytic dehydrogenation reactor.

10. The process of claim 1 further comprising opening a valve on a bypass line when the measured internal differential pressure exceeds the predetermined limit to bypass the second portion of the hydrocarbon-containing feed stream around the select catalytic reactor.

\* \* \* \* \*